United States Patent [19]

Hagiwara et al.

[11] Patent Number: 4,929,431
[45] Date of Patent: May 29, 1990

[54] PROCESS FOR PRODUCING AMORPHOUS ALUMINOSILICATES

[75] Inventors: Zenji Hagiwara, Shiga; Satoshi Ando, Osaka; Saburo Nohara, Hyogo, all of Japan

[73] Assignees: Hagiwara Research Corp., Shiga; Kanebo Ltd., Tokyo, both of Japan

[21] Appl. No.: 83,710

[22] Filed: Aug. 10, 1987

Related U.S. Application Data

[63] Continuation-in-part of Ser. No. 899,026, Aug. 22, 1986, abandoned.

[30] Foreign Application Priority Data

Aug. 23, 1985 [JP] Japan ................................ 60-185634
Aug. 23, 1985 [JP] Japan ................................ 60-185635

[51] Int. Cl.$^5$ .............................................. C01B 33/26
[52] U.S. Cl. .................................................. 423/328
[58] Field of Search ......................... 423/328, 329, 330

[56] References Cited

U.S. PATENT DOCUMENTS

| | | | |
|---|---|---|---|
| 2,040,811 | 5/1936 | Nikitin | 424/140 |
| 2,066,271 | 12/1936 | Irwin | 210/764 |
| 2,512,053 | 6/1950 | Calmon | 423/328 |
| 2,990,247 | 6/1961 | Conrad et al. | 424/155 |
| 3,114,695 | 12/1963 | Rabo et al. | 423/328 |
| 3,228,784 | 1/1966 | Mays et al. | 423/328 |
| 3,382,039 | 5/1968 | Calmon et al. | 423/328 |
| 3,476,692 | 11/1969 | Hoffmann | 424/155 |
| 3,514,270 | 5/1970 | Tomita | 423/329 |
| 3,582,379 | 6/1971 | Hackbarth et al. | 423/328 |
| 3,783,125 | 1/1974 | Ondrey et al. | 208/191 |
| 4,126,574 | 11/1978 | Reinwald | 252/179 |
| 4,264,319 | 4/1981 | Plapper | 8/94.26 |
| 4,284,580 | 8/1981 | Logan | 260/428.5 |
| 4,323,475 | 4/1982 | Ball | 252/373 |
| 4,525,410 | 6/1985 | Hagiwara | 428/198 |

FOREIGN PATENT DOCUMENTS

| | | |
|---|---|---|
| 0097512 | 1/1984 | European Pat. Off. |
| 1068232 | 11/1959 | Fed. Rep. of Germany |
| 2352265 | 4/1975 | Fed. Rep. of Germany |
| 1061158 | 4/1954 | France |
| 2237839 | 2/1975 | France |
| 0162418 | 12/1980 | Japan .................... 423/328 |
| 576971 | 4/1946 | United Kingdom |
| 1232429 | 5/1971 | United Kingdom ........... 423/328 |

OTHER PUBLICATIONS

Taki Kagaku K.K., "Preparing of Amorphous Aluminosilicate", *Patent Abstracts of Japan*, vol. 7, No. 277 (C–199), 1422, Dec. 9, 1983, JP–A–58 156 527, Sept. 17, 1983.

*Primary Examiner*—John Doll
*Assistant Examiner*—R. Bruce Breneman
*Attorney, Agent, or Firm*—Browdy and Neimark

[57] ABSTRACT

There is disclosed a process for producing an amorphous aluminosilicate having the formula:

$$2Na_xO \cdot Al_2O_3 \cdot ySiO_2$$

(wherein x is a number between 0.6 and 1.8 inclusive; and y is a number between 1.3 and 7 inclusive); which comprises:

a step of maintaining an alkali solution (Solution-C), the alkalinity of which is within the range of 1.2–3.5N under stirring;

a step of adding a sodium aluminate solution (Solution-A) containing free alkali and sodium silicate solution or colloidal silica solution (Solution-B) containing free alkali to the Solution-C, separately to prepare a slurry which contains an amorphous sodium aluminosilicate in the form of finely divided particles which are only slightly soluble in water; and a step of aging the slurry, characterized in that the addition of Solution-A and Solution-B into Solution-C is carried out so that the Si/Al ratio in the resultant mixture is kept within the range of 0.7 to 7.6 during and after the addition, and mixing effected at 55° C. or lower, and Solution-A and Solution-B are prepared so that both the alkalinity of the aqueous solution phase during the formation of the slurry and during the maturing is kept within ±0.30N of the alkalinity of Solution-C.

5 Claims, 5 Drawing Sheets

PROCESS FOR PRODUCING AMORPHOUS ALUMINOSILICATES

This application is continuation-in-part application of U.S. Ser. No. 899,026 filed on Aug. 22, 1986 now abandoned.

BACKGROUND OF THE INVENTION

The present invention relates to a novel process for producing an amorphous aluminosilicate. Particularly, this invention relates to a process for producing an amorphous aluminosilicate in the form of porous fine particles having ion exchanging ability; a process for producing the same economically; a process for ion-exchanging the sodium ion of the aluminosilicate with another ion; and a process for producing a filler material in the form of fine particles.

This fine divided amorphous aluminosilicate composition of the present invention has poor hygroscopicity and good dispersing quality, so it is suitable as a filler from the viewpoint of its physical and chemical properties. The filler of this invention can be used as a filler for paper, fibers, plastics, natural rubbers, synthetic rubbers, pigments, coating agents and the like.

The present aluminosilicate is only slightly soluble in water and has good thermal resistance, good waterproofness and considerable ion exchanging ability as mentioned in the following. Furthermore, the present aluminosilicate has good properties for selectively adsorbing a monovalent cation, such as ammonium ion, potassium ion or the like, a divalent cation, such as a calcium ion and magnesium ion or the like, so the aluminosilicate can be used as an ion exchanging agent for inorganic materials.

SUMMARY OF THE INVENTION

The present inventors have made research on the economical synthesis of an amorphous aluminosilicate and technique for making this compound finer. As a result, we have found that aluminosilicate having specific composition and less hydrophilicity can be deposited by adjusting certain factors which participate in the reaction and that the cation exchanging ability of the aluminosilicate can be enlarged.

This invention relates to a process for producing an amorphous aluminosilicate having the formula:

$$xNa_2O \cdot Al_2O_3 \cdot ySiO_2$$

(wherein x is a number between 0.6 and 1.8 inclusive; and y is a number between 1.3 and 7 inclusive); which comprises:

a step of maintaining an alkali solution (Solution-C), the alkalinity of which is within the range of 1.2–3.5 N under stirring;

a step of adding a sodium aluminate solution (Solution-A) containing free alkali and sodium silicate solution or colloidal silica solution (Solution-B) containing free alkali to the Solution-C, separately to prepare a slurry which contains an amorphous sodium aluminosilicate in the form of finely divided particles which are only slightly soluble in water; and a step of aging the slurry, characterized in that the addition of Solution-A and Solution-B into Solution-C is carried out so that the Si/Al ratio in the resultant mixture is kept within the range of 0.7 to 7.6 during and after the addition, and mixing effected at 55° C. or lower, and Solution-A and Solution-B are prepared so that both the alkalinity of the aqueous solution phase during the formation of the slurry and during the maturing is kept within ±0.30 N of the alkalinity of Solution-C.

This invention relates to a process for producing an amorphous aluminosilicate having the formula:

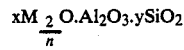

(wherein M is a member selected from the group consisting of potassium, lithium, calcium, magnesium, cobalt (II), iron (II), nickel (II) and ammonium ion; n is the valence of M; x is a number between 0.6 and 1.8 inclusive; and y is a number between 1.3 and 7 inclusive); which comprises ion-exchanging all or part of the Na in the sodium aluminosilicate of claim 1 with M by using a solution containing one or more of these metal ions.

This invention also relates to a process for producing a novel, finely divided active material having poor hygroscopicity which is suitable as a filler.

BRIEF EXPLANATION OF THE DRAWINGS

FIG. 1-A is an X-ray diffraction pattern of the present amorphous aluminosilicate;

FIG. 1-B is an X-ray diffraction pattern of Control Test's aluminosilicate;

In FIGS. 6 and 7, the length of the reversed white portion is 1 μm.

DETAILED DESCRIPTION OF THE INVENTION

Figure 1B:
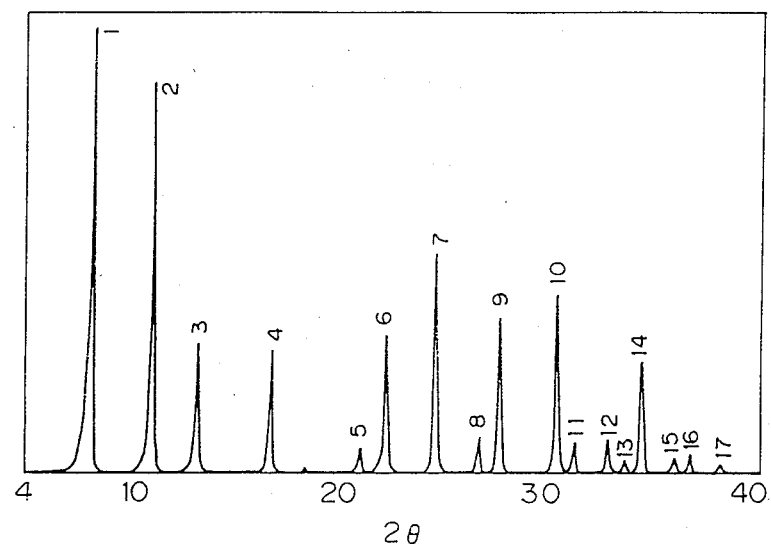
FIG. 1 is an X-ray diffraction pattern of dried powder obtained in Example 2 and Control Test 1.

Preferably the amorphous aluminosilicate obtained by the present invention is porous and has a specific surface area (SSA) of at least 5 m²/g (on a dry basis). According to the process of the present invention, amorphous aluminosilicates having a large SSA ranging from several tens to several hundreds square meter per gram can be readily obtained. The aluminosilicates as synthesized are in the form of fine particles in a slightly hydrous state. As already mentioned, the synthesized product is amorphous (completely amorphous when examined by X-ray diffraction or under an electron microscope). According to the method of synthesis of the present invention, fine grains having the composition represented by $0.6–1.8Na_2O \cdot Al_2O_3 \cdot 1.3–7SiO_2$ (practically insoluble in water) are obtained. The present inventors confirmed that the Na in the compound has an ion-exchanging ability and can be readily displaced by a mono- or divalent-metallic ion that is illustrated by a cation such as potassium, lithium, ammonium ($NH_4^+$), iron (II), magnesium (II), calcium (II), cobalt (II) or nickel (II). The degree of displacement of Na by these metallic ions depends on such factors as the state of valence and the size of hydrated ions. The amorphous aluminosilicate (M=Na; true specific gravity≈2) having the composition specified above which is obtained by the method of synthesis of the present invention has an extremely small particle diameter and the average particle diameter (Dav) as measured under examination with a scanning electron microscope (SEM) is no larger than 0.5 μm. The value of Dav varies with the reaction conditions used in the synthesis of the aluminosilicate but in a typical case Dav is no greater than 0.3 μm. The amorphous aluminosilicate obtained by the method of synthesis of the present invention is filtered by, for example, a centrifuge or a filter press, washed with water to remove the free alkali from the solid phase, dried by heating at 100°–110° C., and ground to the final product. During the steps of filtering and drying, some of the primary fine particles, of which the amorphous aluminosilicate is composed, agglomerate to form larger secondary particles, which can be reduced in size by disintegration or grinding with an appropriate apparatus such as a grinder by the soft or wet method. By employing these procedures, the amorphous aluminosilicate of the present invention can be readily processed into fine particles having a Dav of no larger than 6 μm, typically between 0.01 and 1 μm, as measured by the photo-extinction method.

The preferable production of the amorphous aluminosilicate of the present invention are explained in the following:

An alkali solution (Solution-C) the alkalinity of which is within the range of 1.2 to 3.5 N is maintained under stirring. Into Solution-C are separately added a predetermined amount of a sodium aluminate solution (Solution-A) containing free alkali and a predetermined amount of a sodium silicate solution or colloidal silica solution (Solution-B) containing free alkali, so as to prepare a slurry which contains an amorphous aluminosilicate (principal component: $Na_2O\text{-}Al_2O_3\text{-}SiO_2$) constituted by finely divided particles which are only slightly soluble in water. Then, the slurry is aged to produce an amorphous aluminosilicate. In this method, the addition of Solution-A and Solution-B into Solution-C is carried out so that the Si/Al ratio in the resultant mixture may be kept within the range of 0.7 to 7.6 during and after the addition, and the mixing is effected at 55° C. or lower. In addition, Solution-A and Solution-B are prepared so that both the alkalinity of the aqueous solution phase during the formation of the slurry and during the maturing is kept within ±0.30 N of the alkalinity of Solution-C as prepared in advance in order to suppress any fluctuation of the alkalinity throughout the process, thereby forming an aluminosilicate of the formula:

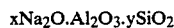

$$xNa_2O.Al_2O_3.ySiO_2$$

wherein Na has ion-exchanging ability; x is 0.6–1.8 and y is 1.3–7 in terms of alumina.

The "alkalinity" referred to in the present invention is measured in the following A definite amount of a sample is taken out from the water phase. If necessary, the sample is diluted with water. Phonolphthalein (an indicator) is added to the sample and then is titrated with a standard hydrochloric acid solution to obtain the alkalinity. In this method, the addition of Solution-A and Solution-B into Solution-C is carried out so that the Si/Al ratio in the resultant mixture may be kept within the range of 0.7 to 7.6 (molar ratio of $SiO_2/Al_2O_3$=1.4 to 15.2) during and after the addition, and the mixing is effected at 55° C. or lower. In addition, Solution-A and Solution-B are prepared so that both the alkalinity of the aqueous solution phase during the formation of the slurry and that during the maturing is kept within 0.30 N of the alkalinity of Solution-C as prepared in advance in order to suppress any fluctuation of the alkalinity throughout the process.

It is preferable that the alkalinity of the slurry is maintained at 1.2–3.5 N. Furthermore, it is preferable that Solution-A Solution-B and Solution-C are adjusted so that the ratio of Na to Al in the slurry is within 1.1–6.7.

As mentioned before, Solution-A used in the present invention is a solution of sodium aluminate containing an excess amount of free alkali. This solution may be readily prepared by adding an excess amount of a strong alkali (sodium hydroxide) to aluminum hydroxide or other appropriate aluminum salt. This solution is the source of alumina ($Al_2O_3$) which is necessary for the synthesis of the amorphous aluminosilicate; at the same time, the solution also serves as a source of supplying part of the alkali ($Na_2O$). Solution-B, as already mentioned, is a solution of sodium silicate or colloidal silica solution containing a free alkali; this solution is the source of silica ($SiO_2$) which is necessary for the synthesis of the amorphous aluminosilicate and, at the same time, it also serves as a source of supplying part of the alkali ($Na_2O$). A suitable example of the Solution-B is a commercial product of sodium silicate or water glass solution (grade No. 3, JIS) or colloidal silica or a combination thereof with an appropriate amount of an alkali. Solution-C which has already been explained is an aqueous solution of sodium hydroxide having a known concentration and an alkalinity which is within the range of 1.2–3.5 N. As already mentioned, it is important to prepare the three feed solutions, A, B and C, in such a manner that the following conditions are met: upon completion of the mixing of the three solutions in their predetermined amounts, the molar ratios of $Na_2O/Al_2O_3$ and $SiO_2/Al_2O_3$ in the mixture are within the ranges of 1.1–6.7 (Na/Al=1.1–6.7) and 1.4–15.2 (Si/Al=0.7–7.6), respectively, and the alkalinity of the resulting slurry solution is at a certain concentration within ±0.30 N of the alkalinity of the preliminarily prepared Solution-C. In the present invention, the three feed solutions are mixed together such that the afore-mentioned conditions are met. A preferable method of mixing is specifically described below: predetermined amounts of Solutions A and B are charged, individually and at predetermined rates, into a reaction vessel which contains Solution-C that maintains agitated state, a certain value of alkalinity within the range of 1.2–3.5 N. In this case, the rates of charging Solutions A and B differ from each other depending upon the concentrations of these solutions and the amounts of their use but preferably the charging of the predetermined amount of Solution-A is completed almost simultaneously with the charging of the predetermined amount of Solution-B. It is essential for the present invention that the compositions and concentrations of the three feed solutions are adjusted at the time of their preparation such that the slurry solution which forms as a result of the mixing of Solutions A, B and C has an alkalinity within the range of 1.2–3.5 N and that the molar ratios of $Na_2O/Al_2O_3$ and $SiO_2/Al_2O_3$ in the mixture are within the ranges of 1.1–6.7 (Na/Al=1.1–6.7) and 1.4–15.2 (Si/Al=0.7–7.6), respectively. In order to eventually obtain the fine particles of a homogenous amorphous aluminosilicate, it is preferable that the three feed solutions are mixed together at a temperature of 55° C. or below, say, in the temperature range of 5°–40° C. Therefore, most preferably, each of the feed Solutions A, B and C is held at 55° C. or below prior to their mixing. As already mentioned, the primary particles in the amorphous aluminosilicate formed at a temperature of 55° C. or below in accordance with the novel mixing method of the present invention have an extremely small average diameter (Dav≦0.5 μm, typically less than 0.1 μm, as measured under examination with SEM). The silicate was verified to have a composition which was within the scope of $0.6–1.8Na_2O.Al_2O_3.1.3–7SiO_2.xH_2O$ on the basis of alumina. For the reasons stated above, the slurry of the amorphous aluminosilicate is preferably formed and ripened at a temperature of 55° C. or below. If slurry formation is effected at temperatures higher than 55° C., the increased temperature of prolonged reaction time will cause part of the resulting amorphous material to crystallize, impairing the homogeneity of the amorphous particles.

It is easy to maintain the alkalinity of the resulting slurry solution within the range specified above and to hold the molar ratios of $Na_2O/Al_2O_3$ and $SiO_2/Al_2O_3$ within the specified ranges during mixing of the feed materials. This can be achieved by adjusting the compositions and alkalinities of the three feed solutions, A, B and C, during preparation of the individual solutions such that constant values of alkalinity and molar ratios are attained when the solutions are mixed together by the procedures described above. In accordance with the method of the present invention for adding Solutions A and B (at 55° C. or below), the slurry mixture will form in such a manner that the alkalinity of the liquid phase is always held substantially constant, and this provides the advantage that the amorphous aluminosilicate can be produced with a minimum variation in its composition. As Solutions A and B are individually charged into the reaction vessel containing Solution-C in a stirred condition in accordance with the unique method of the present invention, the amount of the slurry mixture produced will increase gradually, but the alkalinity in the reaction vessel is held constant until the formation of the slurry and its ripening are completed. This is because the compositions of Solutions A and B are precisely adjusted during their preparation such that they have an alkalinity which is substantially equal to that of Solution-C. What is characteristic of the present invention is that by adding feed Solutions A and B individually to Solution-C and mixing them together with the alkalinity of the mixture being held constant, a slurry solution is obtained that contains extremely fine amorphous aluminosilicate particles which are homogenous and experience a minimum variation in composition. The fine grains of the poorly soluble amorphous aluminosilicate which is obtained by practicing the method of synthesis of the present invention in combination with its unique method of mixing the feed materials have the features that are summarized below.

(i) In the present invention, slurry particles are produced under such conditions that the alkalinity of the aqueous phase and the molar ratios of the feed materials are held constant, so that the resulting amorphous aluminosilicate is homogeneous and is formed of fine particles.

(ii) The fine particles of the amorphous aluminosilicate prepared by the method of the present invention are uniform in shape and the primary particles have an average diameter (Dav) of 0.5 μm or less, typically no larger than 0.3 μm (as measured under examination with SEM).

(iii) The process of the present invention is so designed that homogeneous particles (true specific gravity 2) are formed by not only maintaining a constant alkalinity and temperature but also by avoiding the occurrence of localized concentrations during the mixing of the feed materials. The resulting particles are porous and homogeneous with their composition being within the range of $0.6–1.8Na_2O.Al_2O_3.1.3–7SiO_2$. Since the particles have a specific surface area of at least 5 $m^2/g$, they have the additional advantage of an extremely high activity.

(iv) The fine-grained amorphous aluminosilicate ($Na_2O-Al_2O_3-SiO_2-H_2O$) which is obtained by the method of the present invention will experience a very small degree of variation in its chemical composition and, hence, retains a desirably large ion-exchange capacity.

(v) The fine aluminosilicate particles obtained by the method of the present invention have an extremely high degree of activity and have been found to have characteristics that render them suitable for use as an inorganic filler.

(vi) The fine-grained amorphous aluminosilicate obtained by the method of the present invention are extremely low in hygroscopicity. This shows the suitability of this amorphous aluminosilicate for use as a filler in high-molecular weight materials.

Compositional analyses of the amorphous aluminosilicate obtained by the present invention were conducted by the following procedures and the results of these analyses were used to estimate the formula already set forth in the specification.

Determination of $Na_2O$

An exact amount (0.1–0.2 g) of the amorphous aluminosilicate wa weighed and dissolved in a mixture of water (10 ml) and HCl (2 N, 8–10 ml); water was added to make a total volume of 200 ml; a given amount of the solution was worked up by the standard addition method involving the addition of a predetermined amount of the standard sodium chloride solution, and the $Na_2O$ content was determined by measuring the quantity of sodium by atomic absorption spectroscopy (Na Determined as 589 nm). In measurement of the quantity of sodium, an aqueous solution of potassium chloride was used as an interference inhibitor.

Determination of $Al_2O_3$

An exact amount (0.1–0.2 g) of the amorphous aluminosilicate was weighed and dissolved in a mixture of water (10 ml) and HCl (2 N, 8 ml) to the solution; water was added to make a total volume of 200 ml; a given amount of the solution was taken and a given amount of 0.01 M standard EDTA solution ($Na_2EDTA$: ethylenediaminetetraacetic acid disodium salt) was added, followed by boiling for about 15 minutes; after cooling the solution, 20 ml of an acetic acid/ammonium acetate buffer (60 g $CH_3COOH$ + 77 g $CH_3COONH_4$ + $H_2O$ to make a total volume of 1,000 ml) and 70 ml of 99.5% ethyl alcohol were added to the solution, several drops of a dithizone indicator solution (0.025 g dithizone + 99.5% $C_2H_5OH$ to make a total volume of 100 ml) and reverse titration was conducted with 0.01 M standard zinc acetate solution so as to determine the quantity of aluminum for assaying the $Al_2O_3$ content.

Determination of $SiO_2$

An exact amount (0.1–0.2 g) of the amorphous aluminosilicate was weighed and dissolved in a mixture of water (10 ml) and HCl (2 N, 8 ml) to the solution; water was added to make a total volume of 200 ml, a given amount of the solution was put into a polyethylene beaker and, after addition of one or two drops of hydrofluoric acid (HF), 2 ml of 3 N $H_2SO_4$ and 5 ml of 10 w/v % ammonium molybdate, the mixture was held at 60°–70° C. for 1–2 minutes (on a hot water bath); the heated solution was left to cool for about 10 minutes and a 10 w/v % aqueous solution of tartaric acid (5 ml) and water were added to make a total volume of 100 ml; within 20 minutes thereafter, the content of silicon dioxide was determined by colorimetric analysis involving the measurement of light absorbance at 420 nm.

EXAMPLE 1

This example relates to the preparation of an amorphous aluminosilicate. The starting solutions employed in this example were prepared in the following manner:

Solution-A

To 2.12 kg of aluminum hydroxide [$Al(OH)_3 \cdot xH_2O$, where x is equal to almost 0] were added 3.45 kg of 49% sodium hydroxide solution (density, 1.51) and water. The resulting mixture was heated to dissolve the components. Water was added to the mixture until the total volume amounted to 8.9 liters. The suspended materials were filtered to obtain a clear solution.

Solution-B 0.25 kg of a 49% of sodium hydroxide solution and water were added to 8.7 kg of sodium silicate (JIS No. 3; density, 1.4; $Na_2O$=9.5%, $SiO_2$=29%) until the total volume amounted to 8.9 liters. The suspended materials were filtered to obtain a clear solution.

Solution-C

Water was added to 3.1 kg of a 49% sodium hydroxide solution (density, 1.51) until the total volume amounted to 15.6 liters. The alkalinity of Solution-C was 2.42 N.

Solution-C was charged into a reactor, and heated at 40° C. while stirring at 350 rpm. Solution-A (about 40° C., 8.9 liters) and Solution-B (about 40° C., 8.9 liters) were added to Solution-C over a period of 1 hour and 40 minutes separately. While Solution-A and Solution-B were being added, the molar ratio of $SiO_2/Al_2O_3$ was maintained at 3.38 (Si/Al=1.69). In this example, when mixing of the mixture was finished, the molar ratios of $Na_2O/Al_2O_3$ was 4.43 and the molar ratio of $Na_2O/SiO_2$ was 1.31. The resulting slurry was left at 40° C. for 5 hours while stirring at 250 rpm to age the amorphous aluminosilicate. After aging, the resulting amorphous aluminosilicate was separated from the solution by centrifugal separator. The resulting aluminosilicate was washed with warm water until the pH of the filtrate amounted to 10.5. After washing, the aluminosilicate was dried at about 100° C., and reduced by Brown grinder to obtain 4.1 kg of dried amorphous aluminosilicate.

During the above synthesizing operation, samples were taken out as shown in Tables 1 and 2, and the following tests were effected.

Yield of amorphous aluminosilicate: 4.1 kg
Chemical structure: $1.10 Na_2O \cdot Al_2O_3 \cdot 2.51 SiO_2 \cdot xH_2O$
Average particle size (SEM): Dav=0.2 μm
True specific gravity: 1.9
Specific surface area (SSA): 22 m²/g

TABLE 1

| Alkalinity of Solution | | |
| --- | --- | --- |
| Solution-C | 2.47 N | Alkalinity of preparation |
| When Solution-A and Solution-B were added | 2.47 N | Alkalinity when mixing of starting materials have been completed |
| Aging time | | |
| 2 hrs. | 2.50 N | Alkalinity when the synthesis has been completed |
| 5 hrs. | 2.49 N | |

TABLE 2

| Molar Ratio of Solid Component and Average Particle Size (Dav) | | | |
| --- | --- | --- | --- |
| | Molar ratio | | |
| Aging time | $Na_2O/Al_2O_3$ | $SiO_2/Al_2O_3$ | Dav (μm) |
| 1 hr. | 1.07 | 2.47 | 0.2 |
| 2 hrs. | 1.12 | 2.49 | 0.1 |
| 5 hrs. | 1.10 | 2.51 | 0.2 |

EXAMPLE 2

This example relates to the preparation of an amorphous aluminosilicate. The starting solutions employed in this example were prepared in the following manner.

Solution-A

To 5.05 kg of aluminum hydroxide [$Al(OH)_3 \cdot xH_2O$, where x is equal to almost 0] were added 5.8 kg of a 49% sodium hydroxide solution (density, 1.51) and water. The resulting mixture was heated to dissolve the components. Water was added to the mixture until the total volume amounted to 12.9 liters. The suspended materials were filtered to obtain a clear solution.

Solution-B 0.25 kg of a 49% sodium hydroxide solution and water were added to 11 kg of sodium silicate (JIS No. 3; density, 1.4; $Na_2O$=9.5%, $SiO_2$=29%) until the total volume amounted to 14.5 liters. The suspended materials were filtered to obtain a clear solution.

Solution-C

Water was added to 1.08 kg of a 49% sodium hydroxide solution (density, 1.51) until the total volume amounted to 6.3 liters. The alkalinity of Solution-C was 2.16 N.

Solution-C was charged into a reactor, and heated at 35° C. while stirring at 450 rpm. Solution-A (about 35° C., 12.9 liters) and Solution-B (about 35° C., 14.5 liters) were added to Solution-C over a period of 70 minutes separately. While Solution-A and Solution-B were being added, the molar ratio of $SiO_2/Al_2O_3$ was maintained at 1.79 (Si/Al=0.9). In this example, when mixing of the mixture was finished, the molar ratio of $Na_2O/Al_2O_3$ was 1.99 and the molar ratio of $Na_2O/SiO_2$ was 1.11. The resulting slurry was left at 35° C. for 3 hours while stirring at 350 rpm to age the amorphous aluminosilicate. After aging, the resulting amorphous aluminosilicate was separated from the solution by centrifugal separator. The resulting aluminosilicate was washed with warm water until the pH of the filtrate amounted to 10.6. After washing, the aluminosilicate was dried at about 100° C., and reduced by Brown grinder to obtain 7.39 kg of dried amorphous aluminosilicate.

During the above synthesizing operation, samples were taken out as shown in Table 3; and the following tests were effected.

Yield of amorphous aluminosilicate: 7.39 kg
Chemical structure: $1.03Na_2O.Al_2O_3.3.24SiO_2.xH_2O$
Average particle size (SEM): Dav=0.2 μm
True specific gravity: 2.0
Specific surface area (SSA): 56 m²/g

TABLE 3

| Alkalinity of Solution | | |
|---|---|---|
| Solution-C | 2.16 N | Alkalinity of preparation |
| When Solution-A and Solution-B were added | 2.29 N | Alkalinity when mixing of starting materials have been completed |
| Aging time | | |
| 1 hr. | 2.35 N | Alkalinity when the synthesis has been completed |
| 2 hrs. | 2.30 N | |
| 3 hrs. | 2.25 N | |

The amorphous aluminosilicate obtained in Example 1 contained small amount of water at 100° C. The value of "x" in the formula was 1.2. The ion exchanging ability thereof was 6.9 meq/g (theoretical value). This value was very high. The change in alkalinity during the synthesis was only slight. The alkalinity of the final product was close to that of Solution-C. When the synthesis was effected while suppressing any change in the alkalinity, the molar ratios of $Na_2O/Al_2O_3$ and $SiO_2/Al_2O_3$ were kept substantially constant during aging as shown in Table 2.

The aluminosilicate obtained in Example 2 had an ion exchanging ability of 5.7 meq/g (theoretical value). The alkalinity of Solution-C in Example 2 was 2.16 N; and the alkalinity of the slurry during aging was kept within 2.25–2.35N.

CONTROL TEST 1

This control test shows that when the synthesis was effected under the condition outside those of the present invention, as amorphous aluminosilicate could not be obtained.

This control test was effected on one third the scale of Example 2.

Solution-A

To 1.7 kg of aluminum hydroxide [$Al(OH)_3.xH_2O$, where x is equal to almost 0] were added 1.7 kg of a 49% sodium hydroxide solution (density, 1.51) and water. The resulting mixture was heated to dissolve the components. Water was added to the mixture until the total volume amounted to 4.3 liters. The suspended materials were filtered to obtain a clear solution.

Solution-B

Water were added to 3.7 kg of sodium silicate (JIS No. 3; density, 1.4; $Na_2O=9.5\%$, $SiO_2=29\%$) until the total volume amounted 4.8 liters. The suspended materials were filtered to obtain a clear solution.

Solution-C

Water was added to 0.36 kg of a 49% sodium hydroxide solution (density, 1.5I) until the total volume amounted to 2.1 liters.

PREPARATION OF ALUMINOSILICATE

The total amounts of Solution-A, Solution-B and Solution-C were charged into a reactor. The mixture was stirred at 450 rpm. The mixture was heated to 98° C. and was left at that temperature while stirring for 4 hours and 35 minutes. After the reaction has finished, the solid component was separated from the mixture by centrifugal separator. The resulting aluminosilicate was washed with warm water, until the pH of the filtrate amounted to 10.6. After washing, the aluminosilicate was dried at about 100° C., and reduced by Brown grinder to obtain 2.32 kg of dried reaction product.

Figure 1A:
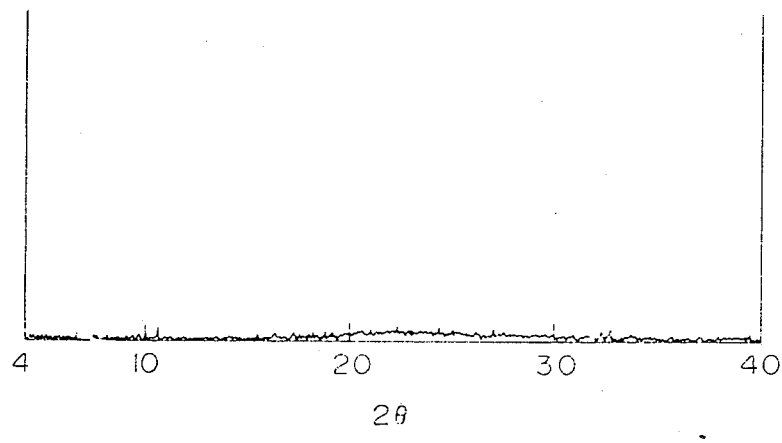

Molar ratio of $SiO_2/Al_2O_3$: 1.79 (Si/Al=0.9)
Molar ratio of $Na_2O/Al_2O_3$: 1.99
Molar ratio of $Na_2O/SiO_2$: 1.11
Yield of A type zeolite: 2.32 kg
Chemical structure: $1.03Na_2O.Al_2O_3.1.92SiO_2.xH_2O$
Average particle size (SEM): Dav=5.3 μm
True specific gravity: 2.04
Specific surface area: 671 m²/g FIG. 1 is an X-ray diffraction pattern of the particles (dried at 100°–110° C.) of Example 2 and Control Test 1. FIG. 1-A is the X-ray diffraction pattern of the aluminosilicate of Example 2. FIG. 1-A shows that the aluminosilicate is amorphous. When it is heated at 500° C., it is still amorphous. FIG. 1-B is X-ray diffraction of the zeolite of Control Test 1. FIG. 1-B shows that it is crystalline.

Figure 6:
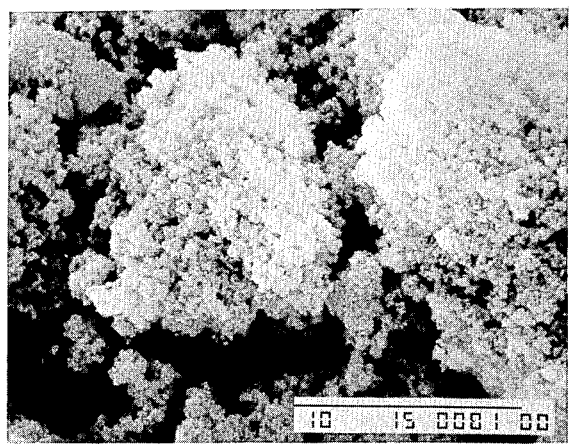
FIG. 6 is an electron micrograph of amorphous aluminosilicate.
Figure 7:
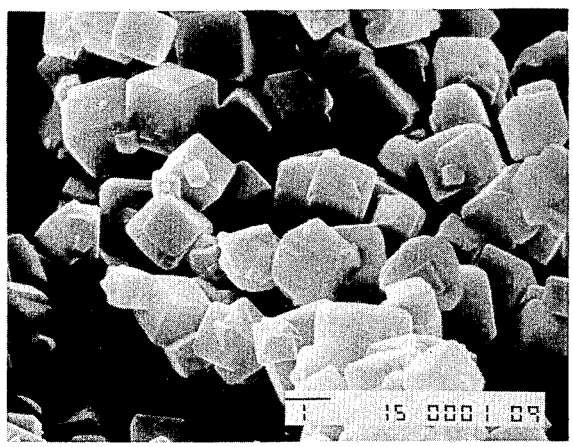
FIG. 7 is an electron micrograph of A-type zeolite aluminosilicate.

FIG. 6 is an electron micrograph of the aluminosilicate of Example 1. It is clear from the micrograph that the aluminosilicate is amorphous. On the other hand, FIG. 7 is electron micrograph of the zeolite of Control Test 1. It is clear from the photograph that the zeolite is crystalline (cubic system) and of A type.

As mentioned above, it is preferable that the reaction temperature is less than 55° C. When the reaction is carried out at a temperature of more than 55° C., crystalline material is partially formed. For example, when the reaction is carried out at 98° C. as in Control Test 1, the resulting product is completely crystalline.

In order to prevent the crystalline portion from being partially formed, it is critical that formation of slurry and aging are carried out at a temperature of less than 55° C.

Figure 2:
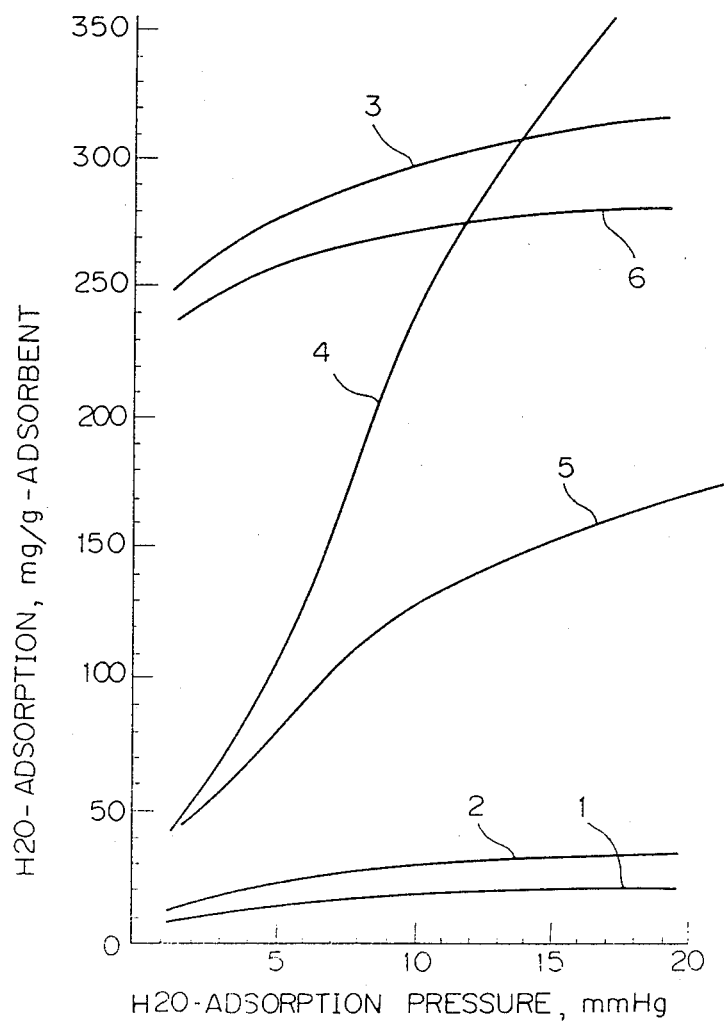
FIG. 2 is a graph showing water-adsorption isotherm (25° C.) of various materials.

FIG. 2 shows water adsorption isotherm (25° C.) of various materials.

Curve 1 . . . aluminosilicate of Example 1
Curve 2 . . . aluminosilicate of Example 2
Curve 3 . . . X type zeolite (Na type)
Curve 4 . . . silica gel ($SiO_2$ gel)
Curve 5 . . . alumina gel ($Al_2O_3$ gel)
Curve 6 . . . activated A type zeolite Adsorbing ability of the aluminosilicates of Examples 1 and 2 is much smaller than that of X type zeolite, silica gel, alumina gel and activated A type zeolite. This shows that the present aluminosilicates are useful as a filler for polymers.

Figure 3:
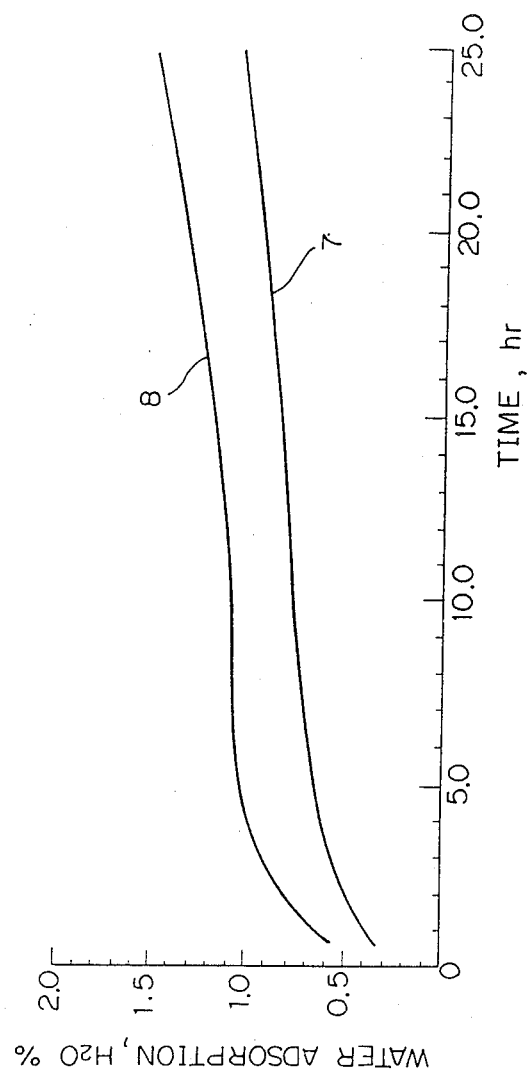
FIG. 3 is a water adsorption curve of the present amorphous aluminosilicate.

FIG. 3 is a graph showing water adsorption with time of activated amorphous aluminosilicate (Na type) at a constant temperature (20° C.±3° C.) and at a constant relative humidity (R.H.=70±5%). Curve 8 shows water absorption of an unhydrous material obtained by heating aluminosilicate of Example 1 (1.10Na$_2$O.Al$_2$O$_3$.2.51SiO$_2$.xH$_2$O) at 500° C. for 1 hour, and curve 7 shows water absorption of unhydrous material obtained by heating aluminosilicate (0.89Na$_2$O Al$_2$O$_3$.2.54SiO$_2$.xH$_2$O) at 500° C. for an hour. Even when 24 hours have passed, the water absorption thereof exhibits preferable value of as less than 2% as.

EXAMPLE 3

This example relates to an ion exchange of the aluminosilicate of Example 2 with ammonium ion. Two hundred and fifty milliliters of 0.1 M NH$_4$Cl solution was added to 100 g of the aluminosilicate (1.03Na$_2$O.Al$_2$O$_3$.3.24SiO$_2$.xH$_2$O) of Example 2. The mixture was left to stand at room temperature for 3 hours and 40 minutes with stirring at 550 rpm to ion-exchange Na of the aluminosilicate with NH$_4$ ion. After the ion-exchanging was finished, the solid component was filtered and washed with water until chloride ion was not eluted. The resulting aluminosilicate was dried for 3 days in a reduced desiccator. Yield of the product was 118 g.

TABLE 4

Ion-Exchange of Amorphous Aluminosilicate (Example 3)

| Ex. | amount of sodium aluminosilicate (dry basis) | amount of NH$_4$Cl added | Ion-exchanging rate of $\overline{NH^{4+}}$ (equivalent ratio) | Yield of product at a reduced pressure |
|---|---|---|---|---|
| 3 | about 100 g | 0.1 M NH$_4$Cl (250 ml) | 0.772 | 118 g |

$\overline{NH_4}$ + $\overline{Na^+}$ = 1 equivalent ratio

As mentioned above, the amorphous aluminosilicate of this invention has great selective absorbance. Example 3 shows ion-exchange of Na ion of aluminosilicate with NH$_4$ ion, Na ion is easily ion-exchanged with NH$_4$ ion. The equivalent ratio of NH$_4$ is 0.772 (the equivalent ratio of Na ion is 0.228).

EXAMPLE 4

This example relates to an ion-exchange of the aluminosilicate of Example 2 with Ca$^{++}$ ion.

Six hundred milliliters of 1.0 M CaCl$_2$ solution was added to 250 g of the aluminosilicate (1.03Na$_2$O.Al$_2$O$_3$.3.24SiO$_2$.xH$_2$O) of Example 2. The mixture was left to stand at room temperature for 6 hours with stirring at 350 rpm to ion-exchange Na of the aluminosilicate with Ca ion. After ion-exchanging was finished, the solid component was filtered and washed with warm water (60° C.) until Ca$^{++}$ ion was not eluted. The resulting aluminosilicate was dried at 100°–110° C. and ground. Yield of the product was 225 g.

TABLE 5

Ion-Exchange of Amorphous Aluminosilicate

| Ex. | Amount of amorphous aluminosilicate (dry basis) | Amount of CaCl$_2$ added | Ion-exchanging rate of $\overline{Ca^{2+}}$ (equivalent ratio) | Yield |
|---|---|---|---|---|
| 4 | about 250 g | 1.0 M CaCl$_2$ (600 ml) | 0.395 | 225 g |

$\overline{Ca^{2+}}$ + $\overline{Na^+}$ = 1 equivalent ratio

Example 4 shows ion-exchange of Na ion of the aluminosilicate with a divalent metal ion. Under the reaction conditions given in Table 5, exchanging ratio of Ca$^{2+}$ + (CA$^{2+}$ represents calcium in a solid phase) is 0.395 equivalent ratio (

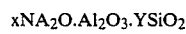

is 0.605 equivalent ratio).

The amorphous aluminosilicate $$(0.6\text{--}1.8\ \underline{M\ _2}\ O.Al_2O_3.1.3\text{--}7\ SiO_2.xH_2O)$$
$$\phantom{xxxxxxxx}n$$

obtained according to this invention has x poor hygroscopicity, can be ground to particle size of 0.01–1 μm and good thermal resistance. For example, it is stable at 600° C., so active, anhydrous, fine particles can be obtained by thermal-treating the aluminosilicate at 200°–600° C. The resulting particles are useful as a filler for paper, fibers, rubbers, synthetic resins, pigments, coating agent and the like.

EXAMPLE 5

This example relates to an ion exchange of the amorphous aluminosilicate with K$^+$ ion.

Two hundred fifty milliliters each of 0.5 M KCl solution (Example 5-A), 2.0 M KCl solution (Example 5-B) was added to 100 g of the aluminosilicate (1.10Na$_2$O.Al$_2$O$_3$.2.51SiO$_2$.xH$_2$O) of Example 1. The mixtures were left to stand at room temperature for 3 hours and 40 minutes with stirring at 450 rpm to ion-exchange Na of the aluminosilicate with K$^+$ ion. After the ion-exchanging was finished, the solid component was filtered and washed with warm water (60° C.) until Cl ion was not eluted. The resulting aluminosilicate was dried at 100°–110° C. and ground. Yield of the product was 96 g (Example 5-A) and 99 g (Example 5-B). The ion exchanging ratio of the resulting exchanged aluminosilicate was 0.254 equivalent ratio (Example 5-A) and 0.453 equivalent ratio (Example 5-B).

TABLE 6

Ion-Exchange of Amorphous Aluminosilicate

| Ex. | Amount of alumniosilicate (dry basis) | Amount of KCl added | Ion-exchanging rate of $\overline{K^+}$ (equivalent ratio) | Yield |
|---|---|---|---|---|
| 5-A | 100 g | 0.5 M KCl (250 ml) | 0.254 | 96 g |
| 5-B | 100 g | 2.0 M KCl (250 ml) | 0.453 | 99 g |

$\overline{Na^+}$ + $\overline{K^+}$ = 1 equivalent ratio

Figure 4:
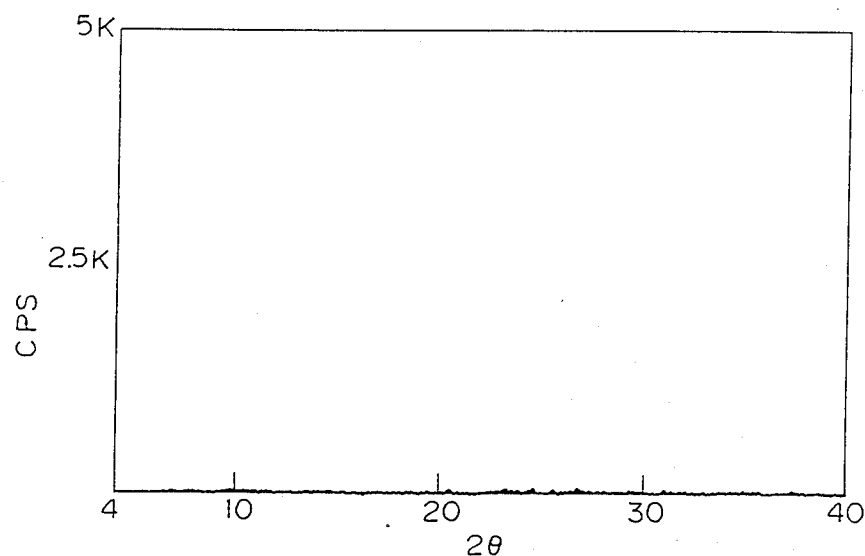
FIGS. 4 and 5 are X-ray diffraction patterns of amorphous Ca and K-partially ion exchanged aluminosilicate, respectively.
Figure 5:
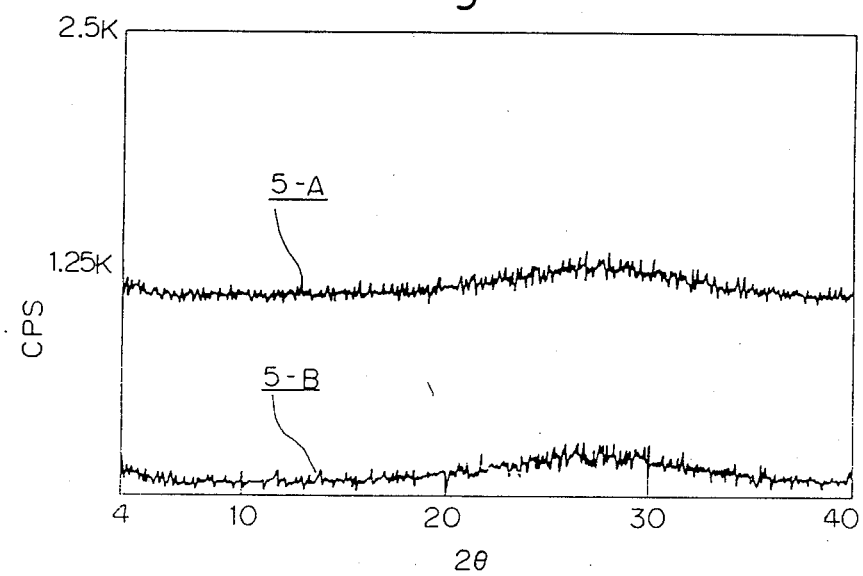

FIG. 4 is X-ray diffraction of amorphous calcium-partially ion-exchanged aluminosilicate of Example 4. FIG. 5 is X-ray diffraction of amorphous potassium-partially ion-exchanged aluminosilicate of Example 5. FIGS. 4 and 5 show that the aluminosilicate obtained in Examples 4 and 5 both are amorphous. Curves 5-A and 5-B in FIG. 5 are X-ray diffractions of Examples 5-A and 5-B, respectively.

What is claimed is:

1. A process for producing an amorphous aluminosilicate having an average particle size of no larger 0.5 μm and a specific surface area of at least 5 m$^2$/g having the formula:

$$xNA_2O.Al_2O_3.YSiO_2$$

wherein x is a number between 0.6 and 1.8 inclusive; and y is a number between 1.3 and 7 inclusive; which comprises:

maintaining an alkali solution (Solution-C), the alkalinity of which is within the range of 1.2-3.5 N under stirring;

adding a sodium aluminate solution (Solution-A), containing free alkali, and sodium silicate solution or collodial silica solution (Solution-B) containing free alkali, to the Solution-C, separately to prepare a slurry which contains an amorphous sodium aluminosilicate in the form of finely divided particles which are only slightly soluble in water; and aging the slurry after completing said addition at 55° C. or lower for at least one hour until ripe, wherein the addition of Solution-A and Solution-B into Solution-C is carried out so that the Si/Al ratio in the resultant mixture is kept within the range of 0.7 to 7.6 during and after the addition, and mixing effected at 55° C. or lower, and Solution-A and Solution-B are prepared so that the alkalinity of the aqueous solution phase during the formation of the slurry and during the aging is kept within ±0.30 N of the alkalinity of Solution-C.

2. A process according to claim 1 wherein Solution-A, Solution-B and Solution-C are adjusted so that the alkalinity of the resulting slurry is within the range of 1.2-3.5 N.

3. A process according to claim 1 wherein Solution-A, Solution-B and Solution-C are adjusted so that the ratio of Na to Al in the slurry is within the range of 1.1-6.7.

4. A process for producing an amorphous aluminosilicate having the formula:

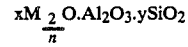

wherein M is a member selected from the group consisting of potassium, lithium, calcium, magnesium, cobalt (II), iron (II), nickel (II) and ammonium ion; n is the valence of M; x is a number between 0.6 and 1.8 inclusive; and y is a number between 1.3 and 7 inclusive; which comprises ion-exchanging all or part of the Na in the sodium aluminosilicate of claim 1 with M by using a solution containing one or more of these metal ions.

5. The process of claim 1, wherein said aging is performed for from 1 to 5 hours.

* * * * *